US012167941B2

(12) United States Patent
Wang et al.

(10) Patent No.: US 12,167,941 B2
(45) Date of Patent: Dec. 17, 2024

(54) SYSTEM AND METHOD FOR SPATIAL POSITIONING OF MAGNETOMETERS

(71) Applicants: COGNITIVE MEDICAL IMAGING LTD., Beijing (CN); INSTITUTE OF BIOPHYSICS, CHINESE ACADEMY OF SCIENCES, Beijing (CN)

(72) Inventors: Fan Wang, Beijing (CN); Yan Zhuo, Beijing (CN); Sijia Yang, Beijing (CN)

(73) Assignees: COGNITIVE MEDICAL IMAGING LTD., Beijing (CN); INSTITUTE OF BIOPHYSICS, CHINESE ACADEMY OF SCIENCES, Beijing (CN)

( * ) Notice: Subject to any disclaimer, the term of this patent is extended or adjusted under 35 U.S.C. 154(b) by 385 days.

(21) Appl. No.: 17/780,750

(22) PCT Filed: Nov. 26, 2020

(86) PCT No.: PCT/CN2020/131747
§ 371 (c)(1),
(2) Date: May 27, 2022

(87) PCT Pub. No.: WO2021/104368
PCT Pub. Date: Jun. 3, 2021

(65) Prior Publication Data
US 2022/0409328 A1    Dec. 29, 2022

(30) Foreign Application Priority Data

Nov. 28, 2019 (CN) .......................... 201911190087.2

(51) Int. Cl.
*A61B 90/00*    (2016.01)

(52) U.S. Cl.
CPC ...... *A61B 90/39* (2016.02); *A61B 2090/3983* (2016.02)

(58) Field of Classification Search
CPC .......... A61B 5/245; A61B 5/369; A61B 5/37; A61B 2090/3983; A61B 5/6803
See application file for complete search history.

(56) References Cited

U.S. PATENT DOCUMENTS 9,791,536 B1    10/2017 Alem et al.
2010/0219820 A1*    9/2010 Skidmore .......... G01R 33/0354
324/247

(Continued)

FOREIGN PATENT DOCUMENTS

CN    1405736 A    3/2003
CN    104380040 A    2/2015

(Continued)

*Primary Examiner* — Gerald Johnson
(74) *Attorney, Agent, or Firm* — Scully, Scott, Murphy & Presser, P.C.

(57) ABSTRACT

A system and a method for spatial positioning of magnetometers. Said system includes: magnetometers, a magnetometer support, first positioning markers, a photogrammetry system, and a controller. The first positioning markers are a non-rotationally-symmetrical pattern. The photogrammetry system includes photographing devices configured to photograph, at at least two of a plurality of photographing sites, first image data of the first positioning markers by means of one or more photographing devices. The controller is configured to receive data of the first image photographed by the photographing devices, calculate spatial positions of the first positioning markers on the basis of pre-obtained system parameters and the first image data, and then calculate spatial positions and spatial orientations of the magnetometers.

20 Claims, 7 Drawing Sheets

(56) References Cited

U.S. PATENT DOCUMENTS

| | | |
|---|---|---|
| 2014/0188422 A1 | 7/2014 | Huber et al. |
| 2018/0313908 A1 | 11/2018 | Knappe et al. |
| 2022/0079527 A1* | 3/2022 | Contreras-Vidal .... A61B 5/398 |

FOREIGN PATENT DOCUMENTS

| | | |
|---|---|---|
| CN | 211178436 U | 8/2020 |
| CN | 112834973 A | 5/2021 |

* cited by examiner

SYSTEM AND METHOD FOR SPATIAL POSITIONING OF MAGNETOMETERS

CROSS-REFERENCE TO RELATED APPLICATIONS

The present application is a national phase entry of PCT International Application No. PCT/CN2020/131747, filed on Nov. 26, 2020, which claims the priority of the Chinese Patent Application No. 201911190087.2, filed on Nov. 28, 2019. The disclosures of PCT International Application No. PCT/CN2020/131747 and Chinese Patent Application No. 201911190087.2 are incorporated herein by reference in its entirety as part of the present application.

TECHNICAL FIELD

The present invention relates to a system and method for spatial positioning of magnetometers.

BACKGROUND

In the field of electroencephalography (EGG) detection, it is usually necessary to install brainwave detecting detectors, such as patch electrodes, around a patient's head. Usually, manual marking or camera array is used to locate the detector.

The magnetic detector in the existing MEG technology takes superconducting quantum interference device (SQUID) as the core device, and its sensitivity is high (about 1 $fT/Hz^{1/2}$), but it needs liquid helium to maintain the superconducting working condition, which leads to very expensive equipment cost and operation cost. A new type of magnetic detector, the Optical-Pumping Magnetometer (OPM), polarizes atomic gas by light beam, and uses the magnetic effect of atomic spin to measure the weak magnetic field. Its measurement accuracy reaches or even exceeds the level that can be achieved by the SQUID magnetometer, and it can work at room temperature without liquid helium cooling. It is small in size and light in weight, and can realize low-cost mass production through semiconductor technology.

In addition, in the actual OPM application, the magnetometers is usually inserted into the patient's helmet to fix the location of the magnetometers. In order to further measure the vector information of the three-dimensional magnetic field, it is necessary to obtain the insertion depth and orientation information of the magnetometers. However, the positioning method of the EGG system can only be used to detect detectors with small thickness and can be regarded as a point in space, such as patch electrodes. Magnetometers are usually large in size, and a complete image cannot be obtained when shooting with a camera array because of the mutual occlusion between magnetometers, so it is difficult to locate the magnetometers and to obtain the spatial orientation information of the magnetometers.

SUMMARY

An embodiment of the present invention provides a system for spatial positioning of magnetometers, which comprises: magnetometers configured to obtain magnetic field data related to magnetoencephalography or biological magnetic fields of other parts; a magnetometer bracket fixedly disposed relative to the head or other body parts of the subject and comprising at least one mounting part with an orientation which allows the magnetometers to be respectively arranged on the mounting part along a specific direction at a first depth; a first positioning marker being a non-rotational-symmetric pattern, and the first positioning marker being respectively disposed in association with the magnetometers; a photogrammetry system, including photographing devices configured to photograph, the first positioning marker to obtain first image data of the first positioning marker, by one or more of the photographing devices, at at least two photographing sites of a plurality of photographing sites; and a controller configured to receive the first image data obtained by the photographing devices and calculate a spatial location and a spatial orientation of the first positioning marker based on pre-obtained system parameters and the first image data, thereby calculating a spatial location and a spatial orientation of the magnetometers.

An embodiment of the present invention provide a method for spatial positioning of magnetometers of the system described above, which includes the following steps: receiving a subject in a photogrammetry system, wherein the subject wears a magnetometer bracket, and at least one magnetometer is arranged on the magnetometer bracket; photographing, by at least one of the photographing devices, at at least two photographing sites of a plurality of photographing sites, a first positioning marker respectively disposed in association with the magnetometers to obtain first image data of the first positioning marker, wherein the first positioning marker is a non-rotationally-symmetric pattern; receiving, by the controller, the first image data obtained by the photographing devices, and identifying, by the controller, the first positioning marker; and calculating a spatial location and a spatial orientation of the first positioning marker based on system parameters and the first image data, thereby calculating a spatial location and a spatial orientation of the magnetometers.

BRIEF DESCRIPTION OF THE DRAWINGS

In order to explain the technical scheme of the embodiments of the present invention more clearly, the drawings of the embodiments of the invention will be briefly introduced below. The drawings are only used to show some embodiments of the invention, but not to limit all embodiments of the invention thereto.

DETAILED DESCRIPTION

Figure 1:
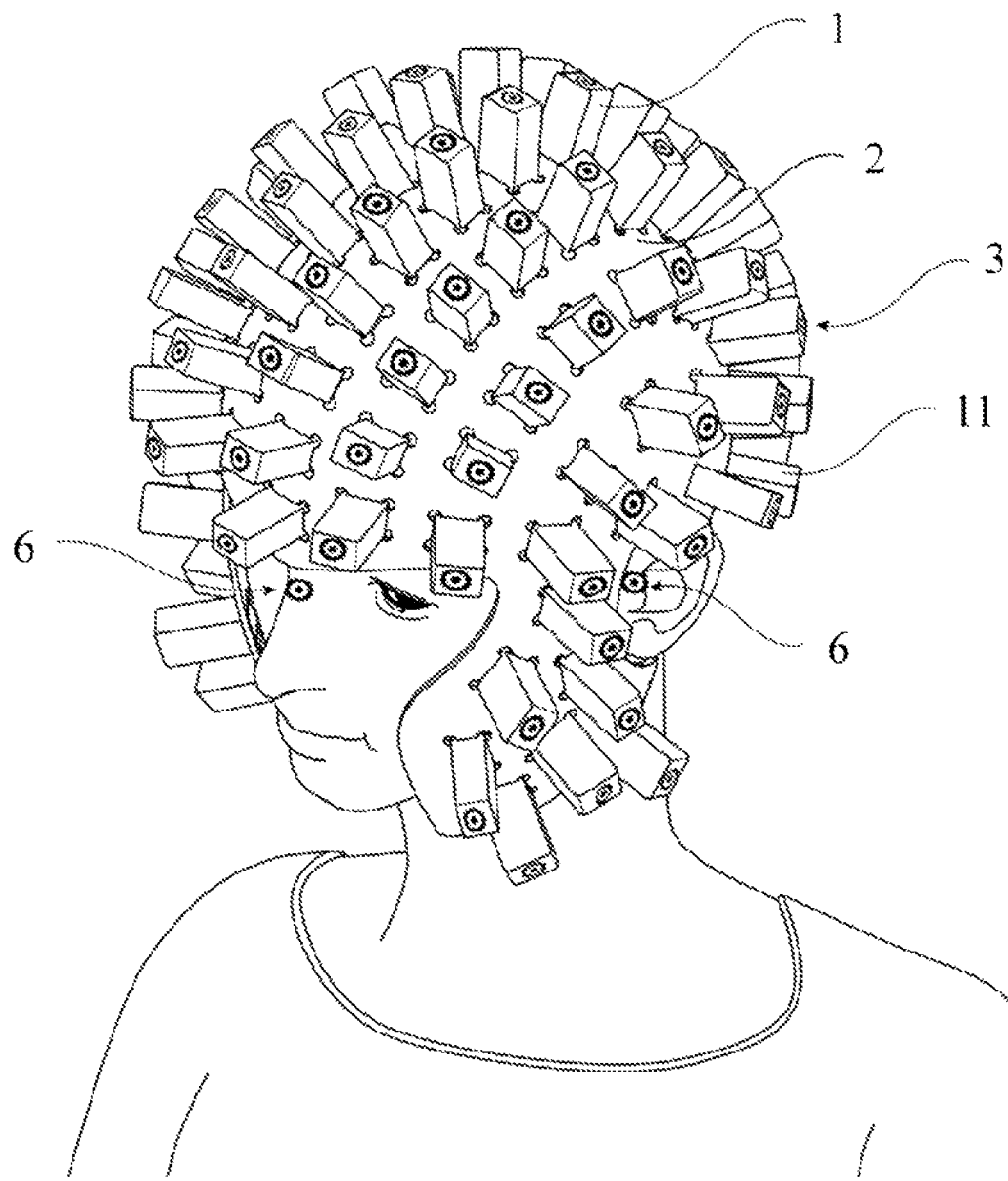
FIG. 1 shows a schematic installation diagram of a magnetometer bracket according to an embodiment of the present invention.

In order to make the purpose, technical scheme and advantages of the technical scheme of the present invention clearer, the technical scheme of the embodiment of the present invention will be clearly and completely described below with reference to the drawings of specific embodiments of the present invention. In the drawings, the same reference numerals represent the same parts. It should be noted that the described embodiments are part of the embodiments of the present invention, but not all of them. Based on the described embodiments of the present invention, all other embodiments obtained by those of ordinary skills in the art without creative labor are within the scope of protection of the present invention.

Unless otherwise defined, the technical terms or scientific terms used here shall have the ordinary meanings as understood by those with ordinary skills in the field to which the invention belongs. Words "first", "second" and the like used in the specification and claims of the patent application of the present invention do not indicate any order, quantity or importance, but are only used to distinguish different components. Similarly, words "one" or "a" and the like don't necessarily mean quantity limitation. Words "comprising" or "including" and the like mean that the elements or objects appearing before the word contain the elements or objects listed after the word and their equivalents, without excluding other elements or objects. Words "connected" or "interconnected" and the like are not limited to physical or mechanical connections, but can include electrical connections, whether direct or indirect connections. "Up", "down", "left" and "right" are only used to indicate the relative positional relationship. When the absolute position of the described object changes, the relative positional relationship may also change accordingly.

In the field of electroencephalography (EGG) or magnetoencephalography (MEG) detection, it is usually necessary to install detectors that detect brainwaves or magnetoencephalography around the head of the subject. However, because the installation location of the detectors is usually on the scalp surface of the subject, it is difficult to detect signals in the brain, hence it is difficult to correlate the signals with the anatomical space and to locate the brain magnetic source. In order to solve this problem, researchers have proposed to combine detector spatial positioning and magnetic resonance imaging (MRI) to obtain the anatomical structure of the subject's brain and the detector spatial position at the same time. This scheme requires the co-registration of the detector spatial data and the MRI.

In EGG, there are mainly four common methods for spatial positioning of detectors:

1. Manual direct measurement, that is, measuring the location between each detector and a fixed marker with a caliper, and calculating the Cartesian coordinates of each detector. This method does not require specific materials or equipment, and has low cost, but it takes a lot of time and manpower to conduct the measurement. At the same time, the measurement accuracy is very low due to human error that can't be ignored.

2. Electromagnetic digital instrument, such as Fastrack system (Polhemus, Colchester, United States), which calculates the location and orientation of a receiver as the receiver moves in the electromagnetic field, the detection accuracy of which can reach 3.6 mm. However, the electromagnetic digital instrument is highly sensitive to the environment, and the metal objects in the environment will change and distort the electromagnetic field, which will affect the integrity of the electromagnetic field, thus greatly affecting the detection accuracy. At the same time, the electromagnetic digital instrument system is expensive and costly.

3. Ultrasonic digital instrument, which measures the distance by measuring the travel time of ultrasonic pulse from the generator to the receiver, so as to calculate the three-dimensional spatial location. However, due to the influence of environmental temperature and humidity, the ultrasonic digital instrument is also highly sensitive to the environment. In addition, similar to the electromagnetic digital instrument, the ultrasonic digital instrument also needs to conduct measurement for the measuring points one by one, which takes a long time.

4. Photogrammetry system, such as Geodesic Photogrammetry System (Electrical Geodesics Inc., United States), which uses a photogrammetry network to measure the spatial location of the objects. The 11 nodes of the photogrammetry sensor network are each equipped with a camera, which can take a single photo at a same time. Then, the system's software is used to triangulate the location of each detector in the two-dimensional photos to generate the three-dimensional spatial coordinates. This method is fast in conducting measurement, during which the subject is allowed move. However, this method can only locate the three-dimensional location point of circular/annular electrodes for the EGG, and it cannot mark the three-dimensional orientation of each detector. In addition, the marker of each detection channel can only be determined by the relative location relationship between the detection channels. If the electrode location is changed or an electrode is replaced, it is necessary to manually mark the detectors in the photo, which will easily lead to operation errors. This system is a visible light illumination system located in the preparation room, which can only be used to calibrate the electrode location in the test preparation stage, but cannot conduct continuous location tracking during the experiment.

The magnetic detector in the existing MEG technology takes superconducting quantum interference device (SQUID) as the core device, and its sensitivity is high (about 1 $fT/Hz^{1/2}$), but it needs liquid helium to maintain the superconducting working condition, which leads to very expensive equipment cost and operation cost. A new type of magnetic detector, the Optical-Pumping Magnetometer (OPM), polarizes atomic gas by light beam, and measures weak magnetic field by using the magnetic effect of atomic spin. The measurement accuracy of an optical-pumping magnetometer based on the spin-exchange relaxation free (SERF) effect reaches or even exceeds the level that can be achieved by the SQUID magnetometer. Also, OPM can work at room temperature without liquid helium cooling. It is small in size and light in weight, and its low-cost mass production can be realized by semiconductor technology.

In addition, because the magnetometers based on SERF effect conducts single-axis or multi-axis vector detection, in the MEG detection field, in order to further measure the three-dimensional magnetic field vector information and make accurate tracing and positioning, it is necessary to obtain the spatial location and spatial three-dimensional direction information of the detector (magnetometer). However, in the existing art, especially in EGG technology, the spatial positioning of the detector mainly focuses on the location positioning and lack the orientation positioning of the detector. Based on this, the present invention proposes a system and method for spatial positioning of magnetometers, specifically, a photogrammetry system and a method based on coded markers.

It should be noted that "spatial positioning" in the present invention refers to spatial location and spatial orientation, and further, "spatial location" in the present invention refers to one or all of the three-dimensional coordinates of an object in space or its relative location with a certain object. The "spatial orientation" of the present invention refers to the vector direction of an object in space with its longitudinal axis taken as the axis and the angle at which the object rotates along the longitudinal axis.

It should be noted that the "non-rotationally-symmetric pattern" in the present invention refers to a pattern that can't coincide with itself after rotating the pattern around any center point by any angle (less than 360 degrees) in a plane.

An embodiment of the present invention provides a system for spatial positioning of magnetometers, the system comprises: magnetometers configured to obtain magnetic field data related to magnetoencephalography or biological magnetic fields of other parts; a magnetometer bracket fixedly disposed relative to the head or other body parts of a subject, and the magnetometer bracket comprising at least one mounting part with an orientation that allows the magnetometers to be respectively disposed on the mounting part along a specific direction at a first depth; a first positioning marker, wherein the first positioning marker is a non-rotational-symmetric pattern, and the first positioning marker is respectively disposed in association with the magnetometers; a photogrammetry system, wherein said photogrammetry system includes photographing devices configured to photograph, by one or more of the photographing devices, at at least two photographing sites of a plurality of photographing sites, the first positioning marker to obtain the first image data the first positioning marker; and a controller, said controller is configured to receive the first image data photographed by the photographing devices and, based on pre-obtained system parameters and the first image data, calculate a spatial location and a spatial orientation of the first positioning marker, thereby calculating a spatial location and a spatial orientation of the magnetometers.

Figure 2:
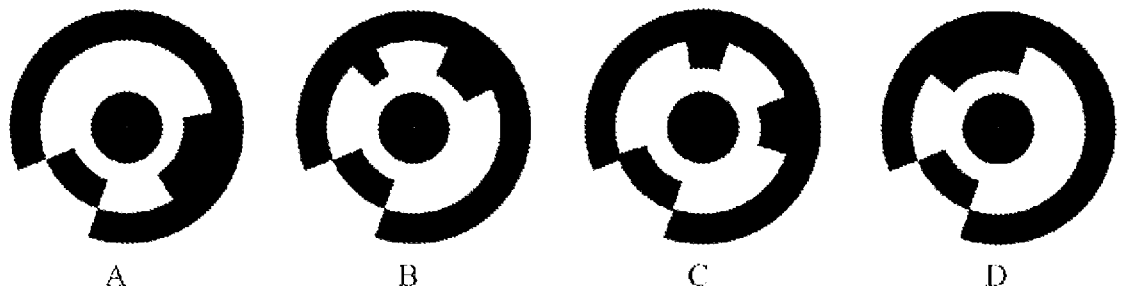
FIG. 2 shows diagrams of a group of coded markers according to an embodiment of the present invention.
Figure 3:
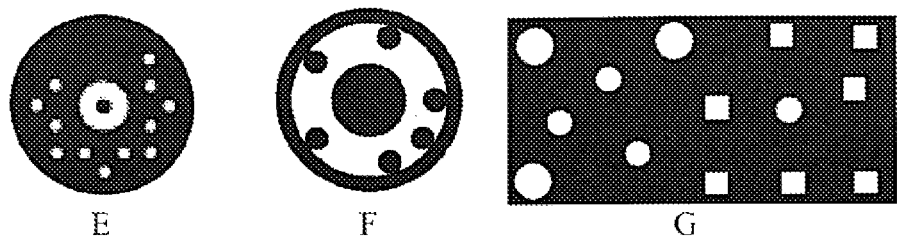
FIG. 3 shows diagrams of coded markers according to another embodiment of the present invention.
Figure 4:
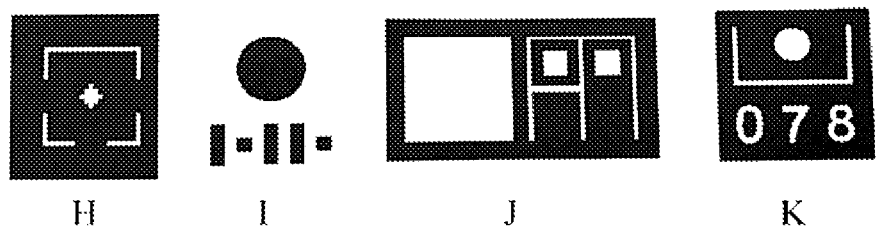
FIG. 4 shows diagrams of coded markers according to yet another embodiment of the present invention.
Figures 5A, 5B:
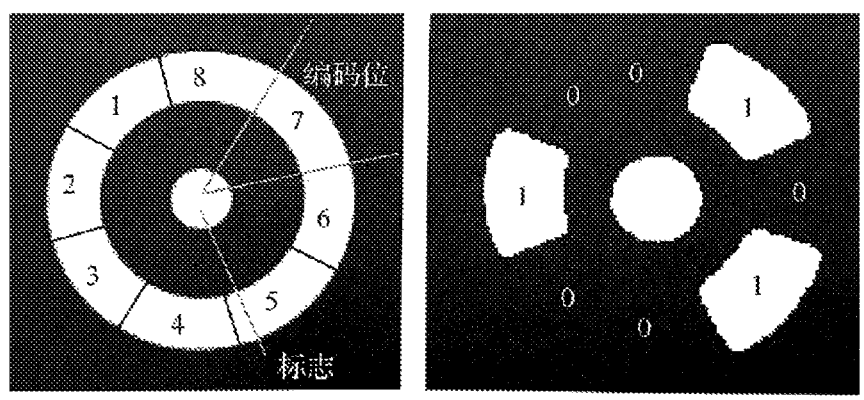
FIGS. 5A and 5B show schematic diagrams of a coding method of coded markers according to an embodiment of the present invention.
Figure 6:
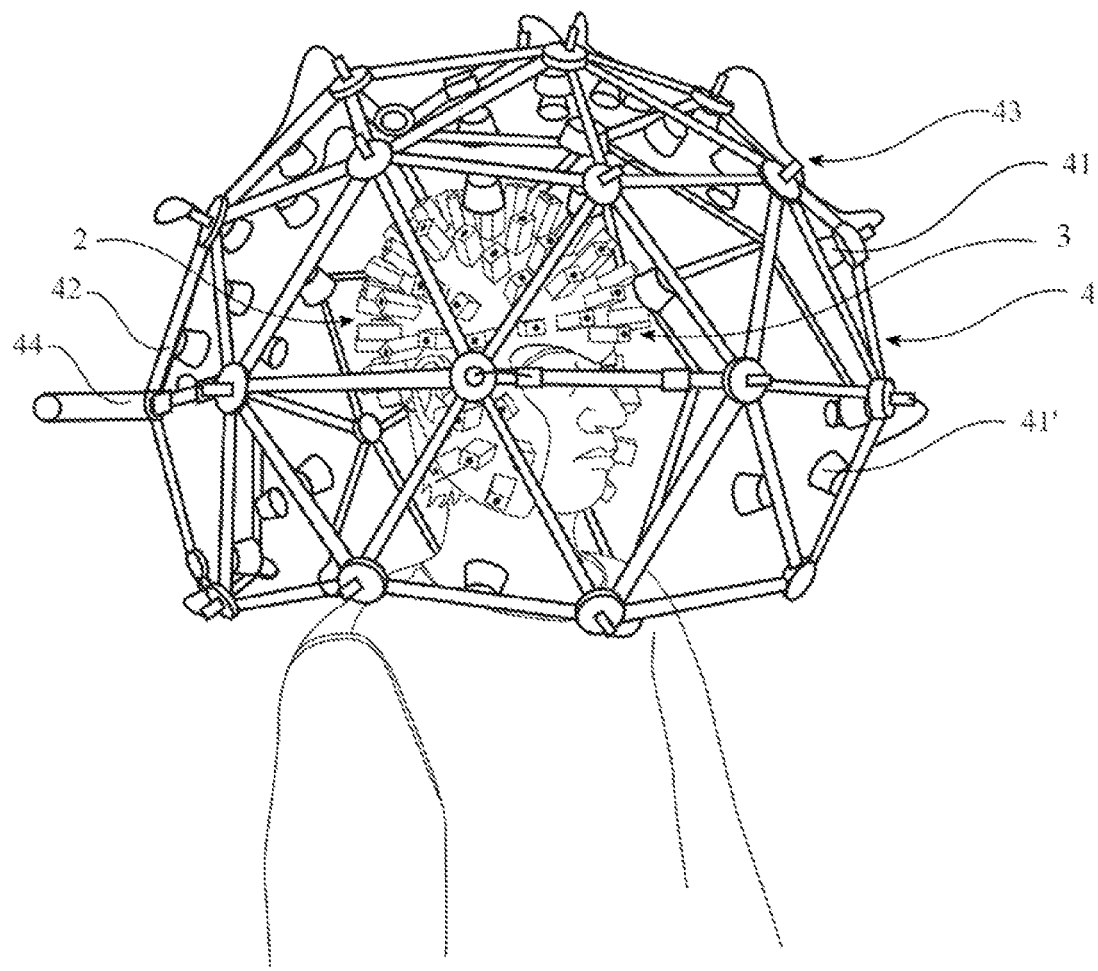
FIG. 6 shows a schematic diagram of a system for spatial positioning of magnetometers according to an embodiment of the present invention.
Figure 7:
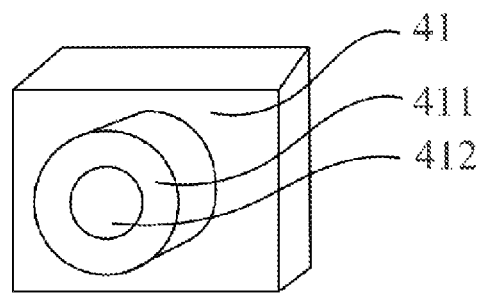
FIG. 7 shows a schematic diagram of a photographing device of the system shown in FIG. 6.

For example, the first positioning marker is fixedly disposed on a magnetometer outer surface (e.g., the end and/or the side) of the magnetometers, on an extension structure rigidly connected with the magnetometers, or on an auxiliary structure of the magnetometer bracket whose location is fixed relative to the magnetometers. Preferably, the first positioning marker is disposed on the outermost end face of the magnetometers, because this location is most easily photographed by the photographing system. FIG. 1 shows a schematic installation diagram of a magnetometer bracket according to an embodiment of the present invention. FIG. 2 shows diagrams of a group of coded markers according to an embodiment of the present invention. FIG. 3 shows diagrams of coded markers according to another embodiment of the present invention. FIG. 4 shows diagrams of coded markers according to yet another embodiment of the present invention. FIGS. 5A and 5B show schematic diagrams of a coding method of coded markers according to an embodiment of the present invention. FIG. 6 shows a schematic diagram of a system for spatial positioning of magnetometers according to an embodiment of the present invention. FIG. 7 shows the schematic diagram of a photographing device of the system shown in FIG. 6.

The system comprises magnetometers 1, a magnetometer bracket 2, a first positioning marker 3 and a photogrammetry system 4. The magnetometers 1 are used to obtain information related to magnetoencephalography. In addition, the magnetometers 1 can also be used to obtain information about the biological magnetic field of other parts, depending on the location where the magnetometers 1 are disposed. As shown in FIG. 1, for example, the magnetometer bracket 2 is in the form of a helmet, which is fixedly disposed relative to the subject's head and includes at least one mounting part (not shown) with an orientation, allowing magnetometers 1 to be respectively disposed on the mounting part in a specific direction and at a first depth.

By way of example, the mounting parts are mounting holes, and the magnetometers 1 is fixedly mounted on the magnetometer bracket 2, so once the mounting is completed, the relative location between the magnetometers 1 and the mounting hole can be fixed and determined.

It should be noted that a detector 11 of the magnetometers 1 is a vector detector, and the detected magnetic field information is vector information, which is different from the traditional EGG detection that only detects scalar signals of the electrode. Therefore, the vector information of the magnetic field detected by the detector 11 needs to be measured.

Optionally, the magnetometer bracket 2 can be rigid or flexible. In this embodiment, the magnetometer bracket 2 is rigid, that is, once it is worn on the subject's head, the relative locations of different magnetometers 1 on the magnetometer bracket 2 will not change easily. The magnetometer bracket 2 can be made of nonmagnetic material, such as photosensitive toughened resin or nano-ceramic materials.

Preferably, the first positioning marker 3 is a first coded marker, which is fixed disposed relative to each magnetometer in a one-to-one correspondence. Said first positioning marker is a planar or three-dimensional structure, and has the invariance of rotation and scaling, so as to maintain the stability and uniqueness of geometric structure at different distances and angles. That is, each first positioning marker 3 has a coded information that corresponds to the fixed magnetometer 1 that this first positioning marker 3 is fixedly disposed on.

By way of example, the system may further include one or more second positioning marker 6, which are fixedly disposed on the head or other body parts of the subject, or on an extension structure which is rigidly connected with the head or other body parts of the subject.

In this embodiment, the first positioning marker 3 is fixedly disposed at the end of the detector 11 of the magnetometer 1. Specifically, the first positioning marker 3 is fixedly arranged on the surface of the end of the detector 11 of the magnetometer 1, and the second positioning markers 6 are fixedly arranged on the head of the subject in the middle of the two eyebrows and in front of the left and right ears, so that the location of the detector 11 of the magnetometers 1 and the location of the subject's head can be marked respectively, so as to carry out the subsequent registration of anatomical sites of body parts with the magnetometer bracket.

Alternatively, depending on the requirements of practical applications, the first positioning marker 3 can also be fixedly arranged at other locations, such as the side of the detector 11 of the magnetometers 1, an extension structure rigidly connected with the magnetometers 1, or an auxiliary structure of the magnetometer bracket 2 with fixed relative location with the magnetometers 1. The present invention is not limited to that. On the premise of ensuring that the coded markers do not occlude each other, it is preferred to arrange more coded markers with larger shapes to obtain better positioning accuracy.

Alternatively, the second positioning marker 6 may not be provided, and the above registration can be achieved by with a three-dimensional image of the body parts from MRI and by using a matching software.

The first positioning marker 3 may be a planar or three-dimensional structure, which has the invariance of rotation and scaling. Also, the first positioning marker 3 is a non-rotationally-symmetric and/or non-axisymmetric pattern, so as to maintain the stability and uniqueness of the geometric structure at different distances and angles. The first positioning marker 3 is a kind of artificial marker with digital coding information, which has unique identity information and can be automatically recognized by image processing and other methods. In this embodiment, the first positioning marker 3 has a planar structure.

The first positioning marker 3 can be at least one of an annular coded marker (also called Schneider coded marker), a dot coded marker, a square coded marker or a number coded marker. FIGS. 2 to 4 exemplarily show the first positioning markers 3 according to the present invention. For example, the first positioning marker 3 may be an annular coded marker as shown by markers A-D in FIG. 2, or a dot coded marker as shown by markers E-G in FIG. 3, or a square coded marker as shown by marker J in FIG. 4, or a number coded marker as shown by marker K in FIG. 4. In addition, the first positioning marker 3 can also be other coded markers with no obvious geometric features as shown by markers H-I in FIG. 4. It should be noted that the above are only shown by way of example, and those skilled in the art can propose other shapes of coded markers based on the teachings of the above examples. In this embodiment, the first positioning marker 3 adopts the annular coded marker.

The encoding principle of the annular coded marker will be described below with reference to FIGS. 5A and 5B. As shown by the markers A-D in FIG. 2, the annular coded marker is mainly composed of a center positioning marker and code bits around it, which can be either banded or dotted. The code bits are distributed on concentric circles with the center positioning marker as the center, and the coding capacity can be increased by increasing the number of concentric circles or the number of code bits on a same circle. The annular coded marker needs to reserve a part of the area as the code reading reference, for example, the lower left area of the annular coded marker shown by markers A-D in FIG. 2. The annular coded marker adopts the principle of binary coding, that is, 0 and 1 coding. Each coded marker has a unique number corresponding to it.

As shown in FIG. 5A, the center positioning marker is surrounded by a circle with a unique code, and the coded circle is divided into n equal parts at equal angles (referred to as n-bit code), each equal part is called a code bit, and each code bit can be regarded as a binary bit, black indicating 0, white indicating 1, and each bit can be 0 or 1, as shown in FIG. 5B. Among them, represents an 8-bit code, so that each coded marker consists a total of eight bits of binary numbers. According to the rotation invariance requirement of the code, each code bit can be used as the first bit of the 8-bit binary number. For each specific marker, there are eight binary numbers corresponding to the 8-bit code. Because each coded marker can only have one unique numerical identity, the minimum value among its corresponding decimal numbers is used as the coded number of the coded marker.

In order to determine the code reading starting position of the coded information, the location of the center O and the radius R can be obtained by fast Hough transform. With O as the center and 2.5R as the radius, the gray value can be read clockwise or counterclockwise and converted into binary code.

Now, if the code bits are combined clockwise, the eight binary numbers corresponding to the code shown in FIG. 5B are: 00100101, 01001010, 10010100, 00101001, 01010010, 10100100, 01001001, and 10010010. Among the eight binary numbers, the decimal number corresponding to 00100101 is the smallest ($00100101_2=37_{10}$), thus the code number corresponding to this coded marker is 37. The present invention is not limited to this. The coding rule can be taking the maximum value, and the code bits can also be combined counterclockwise. Also, the value of n can also be selected according to the actual coding capacity. An appropriate coded marker can be selected, so that it can accommodate a coding capacity of more than 256 channels, and meanwhile having a reasonable and precise positioning reference marker. Through this set of coded marker system, the photogrammetry system 4 can, while recognizing coded marker and calibrating the location of the magnetometers 1, also calibrate the three-dimensional orientation of the magnetometers 1 through perspective projection transformation.

In addition, the first positioning marker 3 may include a reflective material or a stimulated luminescent material to provide sufficient contrast under the illumination light source or excitation light source of the photogrammetry system 4. The reflective material is, for example, glass microbead reflective material, microprism reflective material, etc. The stimulated luminescent material is, for example, fluorescent material, up-conversion luminescent material, phosphorescent material, rare earth luminescent material, etc.

Optionally, the first positioning marker 3 may include an active luminescent material, such as a light emitting diode (LED).

The material of the first positioning marker 3 can be selected according to the illumination light source or excitation light source of the photogrammetry system 4. For example, if the photogrammetry system 4 uses an infrared illumination source, the material of the first positioning marker 3 includes the material reflecting infrared light; if the photogrammetry system 4 uses an excitation light source, the material of the first positioning marker 3 includes the fluorescent material; and if the photogrammetry system 4 does not use an illumination device, the material of the first positioning marker 3 may include the active luminescent material. By using a special illumination light source (such as infrared light) and a coded marker made of the corresponding special reflective material, continuous recording before and during the recording of the marker under special conditions such as dark environment can be achieved.

By way of example, the second positioning marker 6 may have the same graphic characteristics as the first positioning marker 3 and/or be of the same material as the first positioning marker 3.

As shown in FIG. 6, the photogrammetry system 4 can receive the magnetometer bracket 2 therebetween so as to photograph the magnetometer bracket 2, the magnetometers 1 mounted thereon and the first positioning marker 3. The photogrammetry system 4 includes photographing devices 41. The photographing devices 41 are configured to photograph, at at least two photographing sites of a plurality of photographing sites 43, by one or more of said photographing devices 41, the first positioning markers 3 to obtain first image data thereof, and send the obtained first image data to the controller.

By way of example, the photographing device 41 may also be configured to photograph, at at least two photographing sites of the plurality of photographing sites 43, by one or more of the photographing devices 41, the second positioning markers 6 to obtain second image data thereof, and send the obtained second image data to the controller.

The photogrammetry system 4 includes a structural support system 42 for mounting the photographing devices 41. As shown in FIG. 6, the structural support system 42 can be a frame structure that forms a semi-polygon or a hemisphere, so that the structural support system 42 is provided with a plurality of photographing sites 43 in the surface of the hemisphere or other shapes, and each photographing site 43 is fixed with at least one photographing device 41, or at least one photographing device can be moved manually or automatically between different photographing sites, or at least one photographing device is fixed between adjacent photographing sites, so as to realize a fast multi-angle photographing of the coded markers and head/body shapes and so on. In this embodiment, the structural support system 42 is provided with a plurality of photographing sites 43 in a hemispherical surface, each photographing site 43 is fixed with a photographing device 41, and between adjacent photographing sites 43 there is further fixed a photographing device 41'.

By way of example, as shown in FIG. 6, the structural support system 42 may be in the shape of a frame, including a plurality of nodes and connecting piece connecting two adjacent nodes, and the photographing site 43 is arranged on each node. The connecting piece can be fixedly or movably equipped with a photographing device, or no photographing device can be installed.

The photographing device 41 may be a camera or a video camera. As shown in FIG. 7, the photographing device 41 may include an illumination device 411 and a lens 412.

Optionally, the structural support system 42 may further include a position adjusting device 44, which is configured to adjust the position of the photogrammetry system 4 or the structural support system 42. For example, by adjusting the position of the structural support device 42 relative to the magnetometer bracket 2, the lens 412 of the photographing device 41 may get close to or far from the photographed object as required. Alternatively, the position adjusting device 44 can make the entire photogrammetry system 4 away from or close to the subject, so that the photogrammetry system 4 can be set at a position where the subject can be photographed after the subject is ready, and far away from the subject after the photographing, so that the subject can leave. The position adjusting device 44 may include a hinge so that the entire photogrammetry system 4 can pivot, or may include a rail so as to drive the entire photogrammetry system 4 up and/or down and/or to move in other directions.

Optionally, the photogrammetry system 4 may include a reference device (not shown) for calibrating the initial position of the structural support system 42.

Optionally, the photogrammetry system 4 includes a calibration device (not shown) for calibrating the initial location and shooting angle of the photographing device to provide system parameters, so as to further improve the calibration accuracy of the system.

The photographing device 41 and its illumination device 411 can provide sufficient contrast to the first positioning marker 3 to distinguish it from the background object. By photographing the contour of the head and face or other parts of the subject, the magnetometer bracket 2 and the magnetometers 1 at different angles, a three-dimensional model based on one same coordinate system space is established Additional coded markers (second positioning marker 6) can be added to the part other than the magnetometers 1, such as the specific anatomical site of the subject's head or a fixed structure connected with these sites, so as to improve the positioning accuracy of the model reference point. Based on this model, by further recognizing the code characteristics and perspective characteristics of the coded markers connected to the magnetometers 1, the spatial location and orientation information of each magnetometer 1 relative to the above-mentioned three-dimensional model is obtained. Thereafter, by further registering the three-dimensional model and information with the contour obtained by MRI and the like, the location and orientation information of magnetometer 1 in the coordinate system based on anatomical images and the relative location and orientation relationship with the internal structure of the subject's body can be obtained.

In addition, the system according to an embodiment of the present invention may further include a controller (not shown), which stores system parameters obtained in advance. The system parameters may preferably include the focal length of the photographing devices 41, the shooting angle of the photographing devices 41, the spatial location coordinates of the photographing devices 41, the geometric size parameters of the magnetometer and/or the coded information of the first positioning marker 3, etc. However, this is not limiting, and these parameters may also be input by the operator in each measurement. The controller is configured to receive the first image data obtained by the photographing device 41, and calculate the spatial location and spatial orientation of the first positioning marker 3 based on the system parameters and the first image data, thereby calculating the spatial location and spatial orientation of the magnetometers 1.

By way of example, the controller receives the second image data 6 and calculates the spatial location of the subject's head or other body parts based on the system parameters and the second image data 6, so as to achieve the registration of the anatomical site of the subject's head or other body parts with the magnetometer bracket 2.

By way of example, the controller can be a micro controller unit (MCU), a field programmable gate array (FPGA) or a digital signal processor, a CPU, a desktop computer, a workstation, etc. that are common in the art and have data receiving and processing capabilities.

Figure 8:
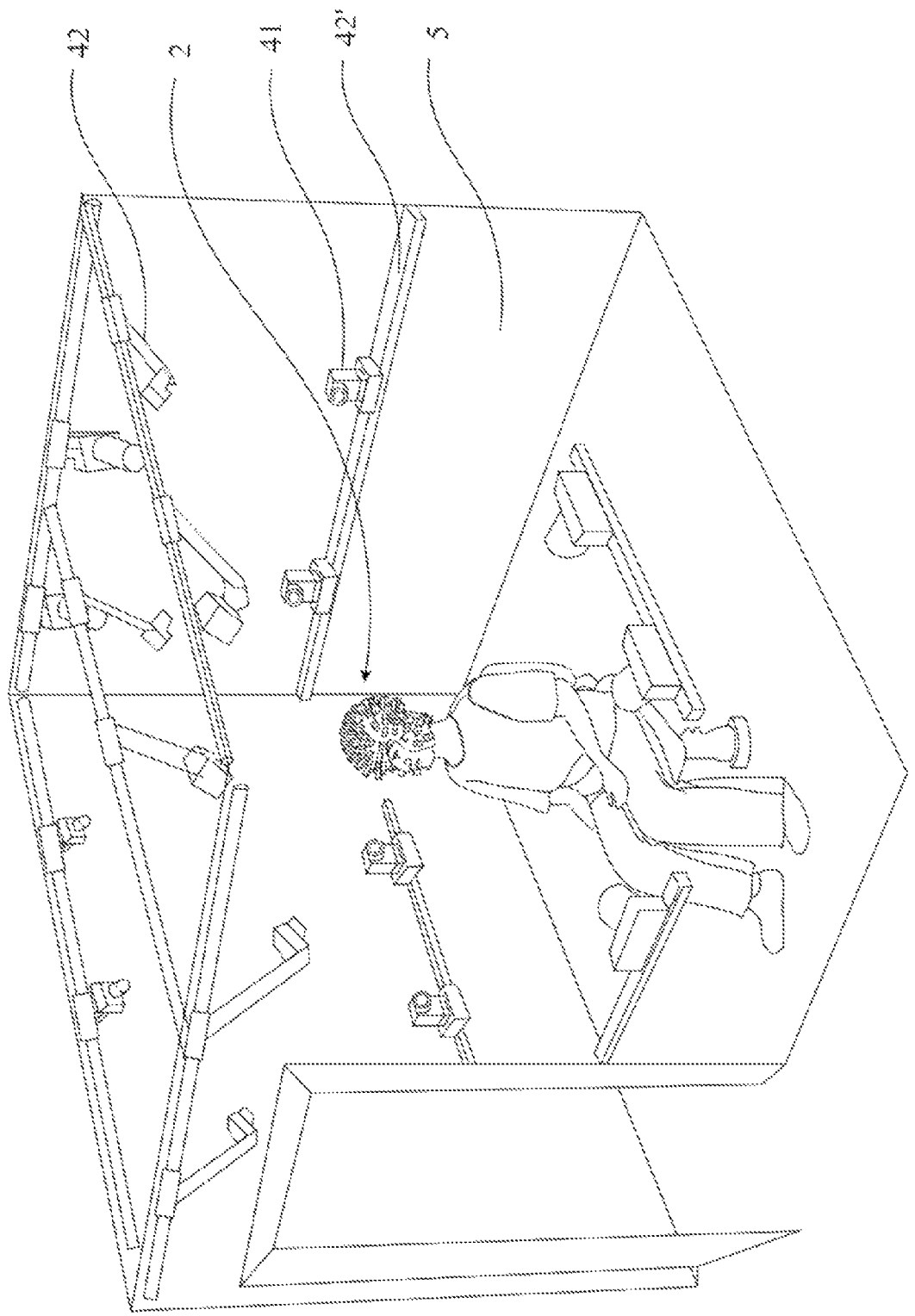
FIG. 8 shows a schematic diagram of a system for spatial positioning of magnetometers according to yet another embodiment of the present invention.

FIG. 8 shows a schematic diagram of a system for magnetometer spatial positioning according to yet another embodiment of the present invention, and the system of this embodiment will be described below with reference to FIG. 8.

Only the differences between this embodiment and the embodiment shown in FIG. 6 will be described below, and features that are similar or identical will not be repeated here.

In this embodiment, the structural support system is fixedly arranged in the shielding room 5. The shielding room 5 can isolate the influence of external magnetic field, electromagnetic field or other interference sources, thus ensuring that the magnetometers 1 will not be disturbed by the change of external magnetic field during measurement. The subject wears a rigid or flexible magnetometer bracket 2 and sits in the shielding room 5.

The structural support system includes, for example, a supporting frame 42 fixedly arranged at the top of the shielding room 5 and a supporting frame 42' fixedly arranged at the sides of the shielding room 5. Photographing devices 41 can be configured to move manually or automatically between different photographing sites, thereby realizing multi-angle adjustable photographing. Therefore, some or all of the photographing devices of the system can continuously track the location of the first positioning marker 3 of the magnetometers 1 and/or the second positioning marker 6 on the body part of the subject during the recording process, so as to continuously record the possible relative location/orientation changes between magnetometers, the relative location/orientation changes between the magnetometer and the subject, and the relative location/orientation changes between the magnetometer and the shielding room.

The above information can be used for a series of purposes, such as the calculation of the pointing field of the magnetometer support 2, the calibration of the magnetometers 11 and the position of the subject's head, and the reduction of the background magnetic field signal. By using a special illumination light source (such as infrared light) and a coded marker made of the corresponding special reflective material, continuous recording before and during the recording of the marker under special conditions such as dark environment can be achieved.

The purpose of decoding and recognizing the coded marker is to determine the digital information of the center positioning marker, that is, the number information of the point, so that the image point with the same name can be found in different images in subsequent calculation, and other non-coded markers can be automatically matched based on the image coordinate information and number information of the center positioning marker.

Figure 9:
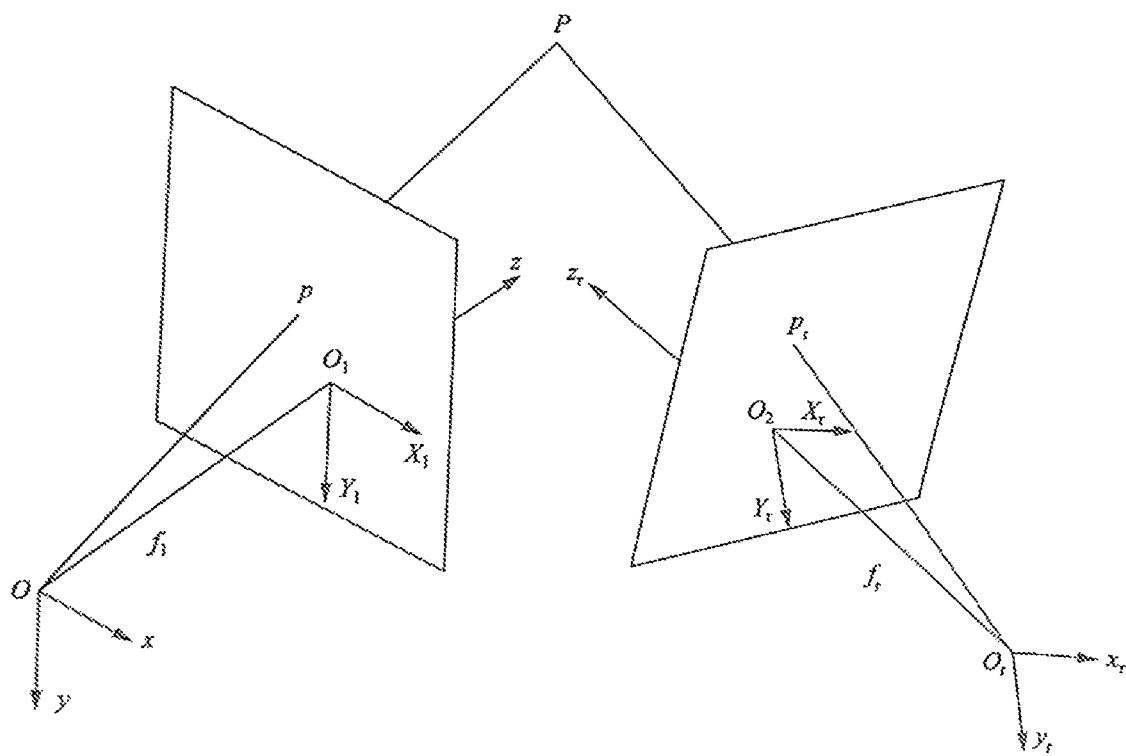
FIG. 9 shows a schematic diagram of three-dimensional coordinate measurement based on two photos of two photographing devices.

FIG. 9 shows a schematic diagram of three-dimensional coordinate measurement based on two photos of two photographing devices as an example of the present invention. That is, the measurement shown in FIG. 9 is to calculate the three-dimensional coordinates of the image points, i.e., the first and/or second positioning markers, in the photos using collinear or coplanar equations and based on two sets of first image data of a first positioning marker photographed by two photographing devices at two photographing sites of a plurality of photographing sites. This measurement principle is widely adopted in the field of computer vision.

Optionally, based on this principle, calculation can also be conducted with the first image data obtained through photographing the first positioning marker by a plurality of photographing devices at more than two photographing sites.

In this embodiment, the image point in the photo, that is, the three-dimensional coordinates of the first and/or second positioning marker, is calculated using the collinear equation. As shown in FIG. 9, let the image space coordinate system O-xyz of the left photographing device coincide with the object coordinate system, with the image plane coordinate system $O_1$-$X_1Y_1$ and the effective focal length $f_1$, and the image space coordinate system of the right photographing device $O_r$-$x_r y_r z_r$, with the image plane coordinate system $O_r$-$X_r Y_r$ and the effective focal length $f_r$. Let the coordinates of the object point P in O-xyz be (X, Y, Z), the coordinates of its corresponding image point p in the left photo in O-xyz is (x, y, $-f_1$), and the coordinates of its corresponding image point pr in the right photo in $O_r$-$X_r Y_r$ is ($x_r$, $y_r$, $-f_r$). Through collinear or coplanar equations (commonly used equations in digital close-range industrial photogrammetry), the following can be obtained:

$$x = -f_1 \frac{X}{Z}$$

$$y = -f_1 \frac{Y}{Z}$$

$$x_r = -f_r \frac{a_1(X - T_x) + b_1(Y - T_y) + c_1(Z - T_z)}{a_3(X - T_x) + b_3(Y - T_y) + c_3(Z - T_z)}$$

$$y_r = -f_r \frac{a_2(X - T_x) + b_2(Y - T_y) + c_2(Z - T_z)}{a_3(X - T_x) + b_3(Y - T_y) + c_3(Z - T_z)} \text{ wherein,}$$

$$R = \begin{bmatrix} a_1 & b_1 & c_1 \\ a_2 & b_2 & c_2 \\ a_3 & b_3 & c_3 \end{bmatrix} \text{ and } T = \begin{bmatrix} T_x \\ T_y \\ T_z \end{bmatrix}$$

are the rotation matrix and the translation matrix between the O-xyz coordinate system and the $O_r$-$X_r Y_r$ coordinate system, respectively.

When the photographing device parameters (including focal length), the image coordinates of the space point to be measured in the left and the right photos, the rotation matrix R and the translation matrix T are known, the three-dimensional coordinates of the space point to be measured can be obtained by combining the above four equations.

Figure 10:
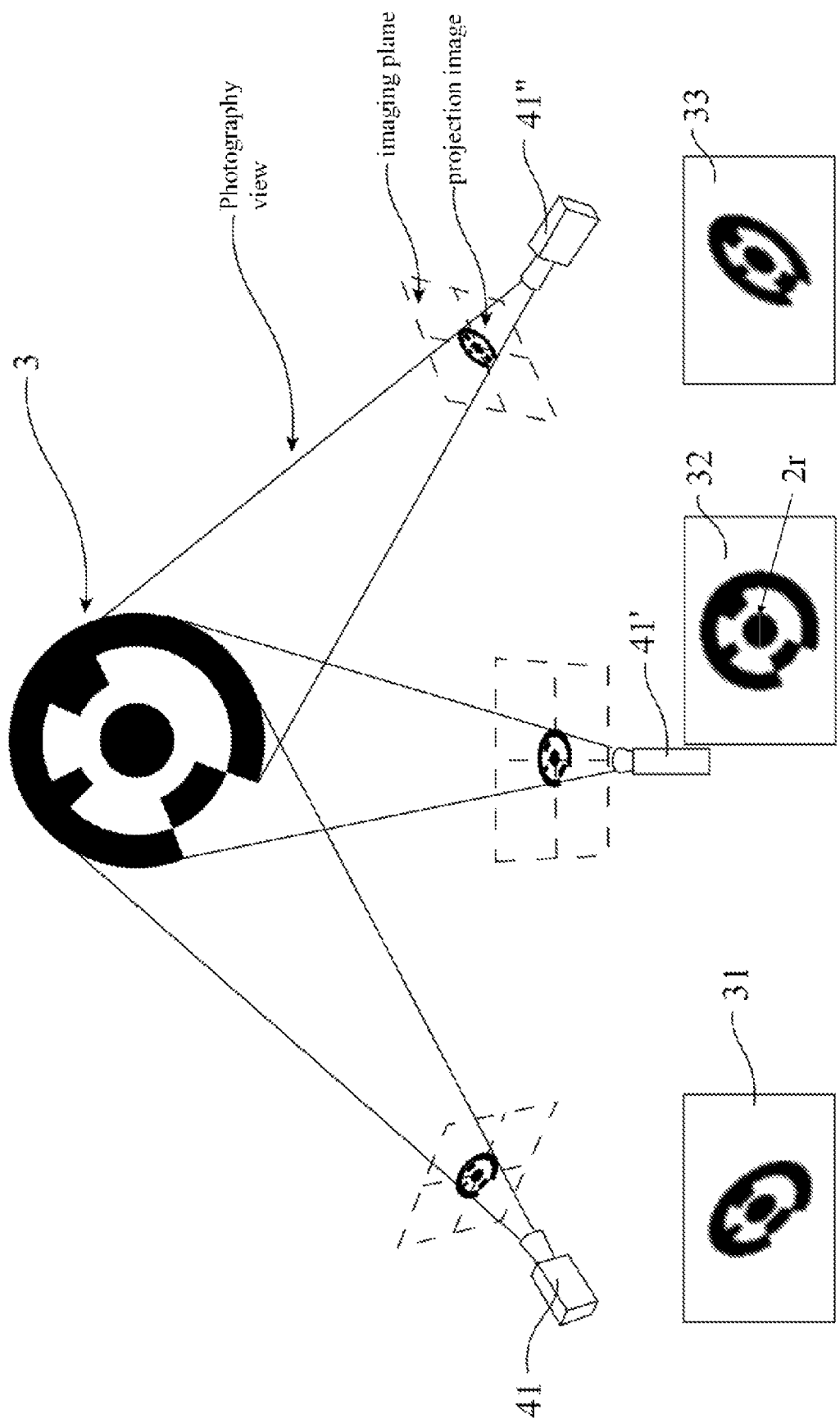
FIG. 10 shows a schematic diagram of the images of a coded marker from different photographing sites.

FIG. 10 shows a schematic diagram of the images of a coded marker from different photographing sites. An example method for calculating the spatial orientation of the coded marker is described below with reference to FIG. 10. As shown in FIG. 10, first positioning markers 31, 32, 33 are images taken by photographing devices 41, 41', 41" from different shooting angles.

For example, the affine parameters of the first and/or second positioning marker can be calculated through affine transformation. In this embodiment, both the first and second positioning markers adopt coded markers. After imaged by the camera lens, the coded marker will generate a projection image on the imaging plane. If the imaging plane is not parallel to the plane where the coded marker is located, the projection image will be distorted, as shown in the first positioning marker 31 and the first positioning marker 33 in FIG. 10. Standardization is to reconstruct the elliptical image after projection distortion into a standard circular image, such as the first positioning marker 32 in FIG. 10. The standardization of the annular coded marker area is to use the five ellipse parameters obtained by ellipse fitting to perform affine transformation around the recognized positioning marker in a certain range, and reconstruct the projected distorted elliptical marker image into a circular image with radius r through affine transformation. The standardization of the coded marker region is the key to the subsequent code recognition. The standardization is completed by the following formula:

$$\begin{cases} x = r \times \frac{(x' - x_0)\cos\theta - (y' - y_0)\sin\theta}{P_1} \\ y = r \times \frac{(x' - x_0)\sin\theta (y' - y_0)\cos\theta}{P_2} \end{cases}$$

Wherein, x', y' are the pixel coordinates within a certain range of the center of the ellipse; $x_0$, $y_0$ are the center coordinates of the standardized circle; $P_1$, $P_2$ are the long and the short half axis lengths of ellipse; X, y are the standardized pixel coordinates; r is the radius of the standardized positioning marker and θ is the angle between the coded marker plane and the imaging plane. The first positioning marker 32 of FIG. 10 shows the standardized image.

The decoding of a coded marker is to convert different code bit distributions of the code band into binary number codes, thereby determining a specific magnetometer number, and since the lens orientation (imaging plane orientation) of the photographing device 41 is known (calibrated), the orientation of the coded marker plane (shooting angle), i.e., the orientation of the magnetometer's end face, can be calculated through the above angle θ (affine parameter), orientation of the lens of the photographing device 41 and the angle between the long axis of the ellipse and the photographing frame of the photographing device. By comparing the rotation angle between the imaged image and the standardized image, that is, the included angle between the position of the coded stripe in the marker after image standardization and the stripe position in the reference image, the rotation angle of the magnetometer along its longitudinal axis can be calculated, and then the triaxial spatial orientation of the magnetometer can be calculated.

To sum up, the basic steps of calculating the spatial location and spatial orientation of a magnetometer based on the coded marker include:

Extracting the outline of the coded marker. Generally speaking, after the coded marker pattern is photographed and imaged by the photographing device, its center positioning marker is an ellipse. According to the image feature extraction algorithm, such as ellipse fitting method or gray weighted centroid method, determining the image coordinates of the ellipse center, and extracting the ellipse target image satisfying the coded marker feature points from the image. Next, segmenting the image using an image segmentation algorithm (such as Canny operator), and extracting the outline information representing different areas from the image. Then, extracting the ellipse contour that meets the conditions by combining the characteristics of size, shape, gray change and position distribution of the coded marker.

The decoding of the coded marker and the decoding steps have been described in detail in the description of the previous embodiment, and they will not be repeated here.

Determining the unique identity of the magnetometer based on the information on the coded marker, thereby classifying and numbering each magnetometer.

Establishing the corresponding matching relationship between the coded markers in a plurality of images shot by one or more of the photographing devices using the numbers of the coded markers. The image matching algorithm based on the coded marker can adopt the slack marker matching algorithm, which needs to determine the similarity and compatibility of the corresponding coded marker. The calculation method for similarity and compatibility is a common algorithm in this field.

After the initial matching is completed, eliminating the mismatching. Mismatching can be eliminated based on the following criteria: similarity criterion, ambiguity criterion or distance constraint error criterion.

After the recognition is completed, the spatial location of each coded marker can be calculated based on collinear equation or coplanar equation, and the spatial orientation of each coded marker can be calculated based on affine transformation (ellipse fitting) and rotation angle. Furthermore, since the geometric parameters and the insertion location (i.e. the location relative to the coded marker) of the magnetometer are known, the spatial location and the spatial orientation of the magnetometer can be calculated.

In other embodiments, if the first positioning marker is a non-rotationally-symmetric marker with no coded information, the steps of recognizing and decoding the coded marker can be omitted in the above steps, while other calculation methods of spatial locations and spatial orientations are similar.

Figure 11:
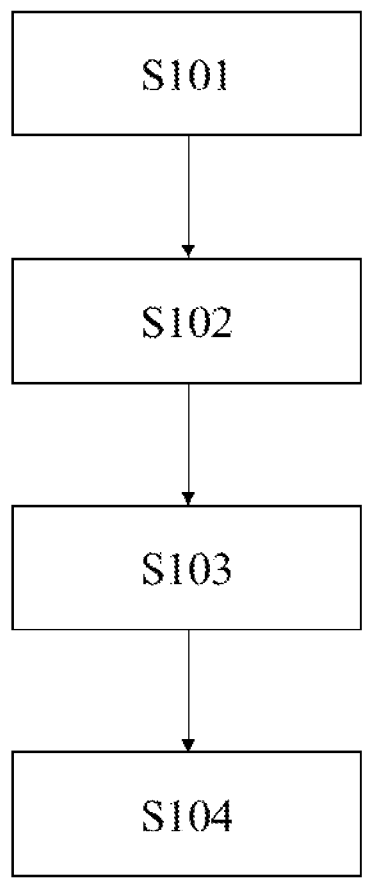
FIG. 11 shows a flowchart of a method for spatial positioning of magnetometers according to an embodiment of the present invention.

FIG. 11 shows a flowchart of a method for magnetometer spatial positioning according to an embodiment of the present invention. The method uses the system for magnetometer spatial positioning according to the above-mentioned embodiment, and the method includes the following steps:

S101. receiving a subject in a photogrammetry system 4, the subject wearing a magnetometer bracket 2, and at least one magnetometer 1 being arranged on the magnetometer bracket 2;

S102. photographing, at at least two photographing sites of a plurality of photographing sites 43, by one or more of the photographing devices 41, a first positioning marker 3 arranged respectively in association with the magnetometers 1 to obtain first image data of the first positioning marker 3, and the first positioning marker 3 being non-rotationally-symmetric patterns;

S103. receiving the first image data obtained by the photographing devices 41 by a controller, and recognizing the first positioning marker 3 by the controller; and S104. calculating the spatial location and the spatial orientation of the first positioning marker 3 based on system parameters and the first image data, and then calculating the spatial location and the spatial orientation of the magnetometers 1.

In step S101, the subject wears the magnetometer bracket 2 on his head or other body parts and is received in the photogrammetry system 4. The magnetometer bracket 2 can be inserted with the magnetometers 1 in advance, or the magnetometers 1 can be inserted after the subject has put on the magnetometer bracket 2. The magnetometers 1 are inserted into a mounting part of the magnetometer bracket 2 or other alternative mounting parts along a insertion direction at a first insertion depth to be installed in place. In the case that the magnetometer bracket 2 is a helmet, the subject can wear the helmet and insert the magnetometers 1 into the mounting part on the helmet and to a predetermined distance from the scalp of the subject. Optionally, the predetermined distance is zero. Then, the position adjusting device 44 can be adjusted so that the subject wearing the helmet is located in the photogrammetry system 4.

In step S102, at at least two photographing sites of the plurality of photographing sites 43, the first positioning marker 3 is photographed by one or more of the photographing devices 41 to obtain first image data. This step can be performed only once, or in real time during the detection of magnetometer 1. When step S103 is performed only once, the obtained image data is a static image. When step S103 is performed in real time, continuous recording and tracking in the detection process can be realized.

In step S103, the controller receives the first image data obtained by the photographing devices 41 and recognizes the first positioning marker. The recognition and decoding methods of the coded marker are as described above, and will not be repeated here. Because different first positioning markers have different coded information, after a certain first positioning marker is recognized, the magnetometers 1 corresponding to this first positioning marker can be recognized. In this way, the recognition and decoding of different magnetometers 1 can be completed.

In step S104, the spatial location and the spatial orientation of the first positioning marker are calculated based on the system parameters and the first image data, and then the spatial location and the spatial orientation of the magnetometer are calculated. Specifically, for a recognized first positioning marker 3, based on the initial position and shooting angle of the photographing devices 41, the three-dimensional coordinates of the first positioning marker 3 and the plane orientation of the coded marker is calculated using the three-dimensional projection algorithm. Also, based on the recognition result, the rotational orientation of the first positioning marker can be calculated, so that the spatial location and orientation of the first positioning marker can be calculated, and then the spatial location and triaxial direction of the magnetometer can be calculated. Meanwhile, the three-dimensional magnetic field vector information can be calculated based on the received magnetic field data of the magnetometer.

Optionally, the method further includes calibrating and/or inputting system parameters. Calibrating system parameters mainly include calibrating the focal length, spatial position and shooting angle of the photographing device 41, as well as inputting the coded information of the first positioning marker 3 and the geometric size parameters of the magnetometer. By way of example, when the system includes a second positioning marker 6, calibrating the system parameters also includes inputting the coded information of the second positioning marker 6. Calibration and/or input of system parameters can be performed each time before the subject receives measurements, or for example at certain time intervals, such as during the daily, weekly or monthly routine maintenance of the system. The coded information of the first positioning marker 3 and the second positioning marker 6 includes original image of the first positioning marker 3 and the second positioning marker 6 which are fixedly arranged, for example, on the end surface of the detector 11 of the magnetometers 1 or on the head of the subject. This image is an undistorted and rotated orthographic image, that is, an image taken from the front.

Specifically, the calibration of the photographing device 41 is realized by a calibration board, which is a common device for calibrating multi-camera industrial photogrammetry systems.

Optionally, the method further includes photographing, at at least two photographing sites at a plurality of photographing sites 43, by one or more of the photographing devices 41, the second positioning marker 6 to obtain the second image data thereof. The second positioning marker 6 may have the same graphic characteristics as the first positioning marker 3 and/or be of the same material as the first positioning marker 3. Therefore, the recognition and decoding method of the second positioning marker 6 is the same as that of the first positioning marker 3. A controller is used to receive the second image data and calculates the spatial location of the subject's head or other body parts based on the system parameters and the second image data, so as to realize the registration of anatomical sites of the subject's head or other body parts with the magnetometer bracket.

Optionally, the method further includes fixedly disposing a structural support system 42 in the shielding room 5 and accommodating the subject in the shielding room 5.

Optionally, the method further includes continuously receiving image data from the photogrammetry system through the controller during the magnetometer measurement process to calculate, record or track the location/orientation change of the magnetometer in real time. The data continuously received during the magnetometer measurement can be used to calculate, record or track the possible location/orientation changes of the magnetometer during the recording process caused by a flexible magnetometer bracket in real time, so as to establish more accurate dynamic three-dimensional process information of the magnetic field. In addition, it can also be used for background noise reduction, motion artifact correction and a series of other post-processing operations.

To sum up, the system and method for magnetometer spatial positioning based on coded marker photogrammetry provided by the present invention have the advantages that only one set of system is needed to simultaneously calibrate the location, direction and the positional relationship relative to human anatomical features of any number of magnetometers, without the need to add an active calibration device to each detector, thus eliminating the risk of electromagnetic interference that the calibration device may cause to magnetometers and greatly saving the cost.

In addition, compared with an active measuring device based on a built-in gyroscope or electromagnetic digital instrument, the system based on the coded marker photogrammetry of the present invention is a passive system, and there is no need to consider the possible electromagnetic interference to the magnetometers. The manufacturing cost of each magnetometer is lower, and the replacement of the magnetometers or measuring devices is faster and simpler. The spatial resolution and angular resolution is higher, and the calibration error is lower. Also, the system can continuously record in the working state of the magnetometers. Compared with other passive calibration methods, the measuring device of photogrammetry optical system based on multiple cameras has a fast calibration speed and conducts measurement in only a few seconds or less, and its efficiency is much higher than that of manual measurement and other passive calibration technologies such as external electromagnetic digital instrument or ultrasonic digital instrument.

Compared with marker-free optical passive calibration methods such as depth camera, hand-held/multi-camera structured light, etc., the system and method provided by the present invention have higher space/orientation measurement accuracy, and can automatically identify the corresponding channel number of each magnetometer based on the coded marker, thus automatically identify the spatial relative location of the magnetometer without the need to arrange the magnetometers according to a specific location correspondence, thus reducing the possibility of misoperation and greatly improving the efficiency of installing and replacing magnetometer.

The exemplary embodiments of the system and method for spatial positioning of magnetometers proposed by the present invention are described in detail above with reference to preferred embodiments. However, it can be understood by those skilled in the art that many variations and modifications can be made to the above specific embodiments without departing from the concept of the present invention. For example, although an algorithm for calculating the spatial location and orientation of magnetometer through positioning markers is described in detail above, the present invention is not limited to this, but any favorable algorithm or simplified method can be adopted, as long as the algorithm can achieve the calculation accuracy required. In addition, various technical features and structures proposed by various aspects of the present invention can be combined in various ways without exceeding the scope of protection of the present invention, which is determined by the appended claims.

What is claimed is:

1. A system for spatial positioning of magnetometers, comprising:

magnetometers configured to obtain magnetic field data related to magnetoencephalography or biological magnetic fields of other parts;

a magnetometer bracket fixedly disposed relative to the head or other body parts of a subject, and the magnetometer bracket comprising at least one mounting part with an orientation allowing the magnetometers to be respectively disposed at the mounting part along a specific direction at a first depth;

a first positioning marker being a non-rotational-symmetric pattern, the first positioning marker being respectively disposed in association with the magnetometers;

a photogrammetry system comprising photographing devices, configured to photograph the first positioning marker to obtain first image data of the first positioning marker, by at least one of the photographing devices, at at least two photographing sites of a plurality of photographing sites; and a controller configured to receive the first image data obtained by the photographing devices, and to calculate a spatial location and a spatial orientation of the first positioning marker based on pre-obtained system parameters and the first image data and thus calculate a spatial location and a spatial orientation of the magnetometers.

2. The system according to claim 1,
wherein the system parameters comprise a focal length of the photographing devices, a shooting angle of the photographing devices, spatial location coordinates of the photographing devices, coded information of the first positioning marker and/or geometric size parameters of the magnetometers.

3. The system according to claim 2,
wherein the first positioning marker is fixedly disposed on an outer surface of the magnetometers, on an extension structure rigidly connected with the magnetometers, or on an auxiliary structure of the magnetometer bracket that is fixed relative to the magnetometers.

4. The system according to claim 3,
wherein the first positioning marker is a first coded marker that is respectively fixedly disposed relative to each magnetometer in a one-to-one correspondence, and the first positioning marker is a planar or three-dimensional structure with invariance of rotation and scaling, so as to maintain the stability and uniqueness of the geometric structure at different distances and angles.

5. The system according to claim 4,
wherein the first positioning marker is at least one of an annular coded marker, a dot coded marker, a square coded marker or a number coded marker.

6. The system according to claim 4, wherein the first positioning marker comprises a reflective material or a stimulated luminescent material to provide sufficient contrast under illumination light source or excitation light source, or wherein the first positioning marker comprises an active luminescent material.

7. The system according to claim 2, wherein the controller is configured to calculate the three-dimensional coordinates of the first positioning marker by collinear or coplanar equations respectively, and to calculate the spatial location of each magnetometer based on the calculated three-dimensional coordinates of the first positioning marker and the geometric parameters of the magnetometers.

8. The system according to claim 2, wherein the controller is configured to:

calculate the affine parameters of the first positioning marker by affine transformation method;

calculate the spatial orientation of the plane where the first positioning marker is located through the affine parameters, the system parameters and the first image data;

calculate a rotation angle of the first positioning marker in the plane where the first positioning mark is located, by comparing the rotation angle between the first image data and the reference image, so as to calculate the spatial orientation of the first positioning marker; and calculate the spatial orientation of the magnetometers according to the geometric parameters of the magnetometers and the spatial orientation of the first positioning marker.

9. The system according to claim 1, further comprising:
at least one second positioning marker being a non-rotationally-symmetric pattern fixedly disposed at the head or other body parts of the subject, or on an extension structure rigidly connected with the head or other body parts of the subject, wherein, the photographing device are configured to photograph the second positioning marker to obtain second image data of the second positioning marker, by at least one of the photographing devices, at at least two photographing sites of a plurality of photographing sites, and the controller receives the second image data and calculates the spatial positioning of the head or other body parts of the subject based on the system parameters and the second image data, so as to realize the registration of anatomical sites of the head or other body parts of the subject with the magnetometer bracket.

10. The system according to claim 9,
wherein the second positioning marker is a second coded marker that is respectively fixedly disposed relative to the head or other body parts of the subject in a one-to-one correspondence.

11. The system according to claim 10, wherein the controller is configured to continuously receive the image data from the photogrammetry system during a measurement process of the magnetometers, to calculate, record or track the location and/or orientation change of the magnetometers in real time.

12. The system according to claim 1, wherein the photogrammetry system further comprises:

a calibration device for calibrating the initial position and shooting angle of the photographing devices; and a structural support system provided with a plurality of photographing sites in a hemisphere or other shaped surface, wherein each photographing site is fixed with at least one photographing device, and/or at least one photographing device can be manually or automatically moved between different photographing sites, and/or at least one photographing device is fixed between adjacent photographing sites.

13. A method for spatial positioning of magnetometers, comprising the following steps:

receiving a subject in a photogrammetry system, wherein the subject wears a magnetometer bracket, and at least one magnetometer is disposed at the magnetometer bracket;

photographing, by at least one of the photographing devices, at least two photographing sites of a plurality of photographing sites, a first positioning marker that is disposed respectively in association with the magnetometers to obtain first image data of the first position marker, wherein the first positioning marker is a non-rotationally-symmetric pattern;

receiving, by a controller, the first image data obtained by the photographing devices, and identifying, by the controller, the first positioning marker; and calculating a spatial location and a spatial orientation of the first positioning marker based on system parameters and the first image data, and then calculating a spatial location and a spatial orientation of the magnetometers.

14. The method according to claim 13, wherein calculating the spatial location of the first positioning marker comprises calculating the three-dimensional coordinates of the first positioning marker by collinear or coplanar equations respectively; and calculating the spatial location of the magnetometers comprises calculating the spatial location of the magnetometers based on the geometric parameters of the magnetometers and the three-dimensional coordinates of the first positioning marker.

15. The method according to claim 13, wherein calculating the spatial orientation of the first positioning marker comprises:

calculating the affine parameters of the first positioning marker by affine transformation method;

calculating the spatial orientation of the plane where the first positioning marker is located through the affine parameters, the system parameters and the first image data;

calculating a rotation angle of the first positioning marker in the plane where the first positioning mark is located, by comparing the rotation angle between the first image data and the reference image, so as to calculate the spatial orientation of the first positioning marker; and calculating the spatial orientation of the magnetometers according to the geometric parameters of the magnetometers and the spatial orientation of the first positioning marker.

16. The method according to claim 13, wherein the first positioning marker is fixedly disposed on an outer surface of the magnetometers, on an extension structure rigidly connected with the magnetometers, or on an auxiliary structure of the magnetometer bracket that is fixed relative to the magnetometers.

17. The method according to claim 16, wherein the first positioning marker is a first coded marker that is respectively fixedly disposed relative to each magnetometer in a one-to-one correspondence, and the first positioning marker is a planar or three-dimensional structure with invariance of rotation and scaling, so as to maintain the stability and uniqueness of the geometric structure at different distances and angles.

18. The method according to claim 13, further comprising:

photographing, by at least one of the photographing devices, at at least two photographing sites of a plurality of photographing sites, a second positioning marker to obtain the second image data of the second positioning marker;

receiving, by the controller, the second image data, and calculating the spatial positioning of the head or other body parts of the subject based on the system parameters and the second image data, so as to realize the registration of anatomical sites of the head or other body parts of the subject with the magnetometer bracket.

19. The method according to claim 18, wherein the second positioning marker is a second coded marker that is fixedly disposed relative to the head or other body parts of the subject in a one-to-one correspondence, and the second positioning marker has the same graphic characteristics as the first positioning marker and/or is of the same material as the first positioning marker, and the method of calculating the spatial location and spatial orientation of the second positioning marker is the same as that of the first positioning marker.

20. The method according to claim 13, further comprising:

continuously receiving, at the controller of the magnetometers, the image data from the photogrammetry system to calculate, record or track the location and/or orientation change of the magnetometers in real time.

* * * * *